US00PP19913P2

(12) United States Plant Patent
Griesbach et al.

(10) Patent No.: US PP19,913 P2
(45) Date of Patent: Apr. 14, 2009

(54) PEPPER NAMED '06C84'

(50) Latin Name: *Capisum annuum*
Varietal Denomination: 06C84

(75) Inventors: Robert J. Griesbach, Ellicott City, MD (US); John R. Stommel, Glenwood, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/006,517

(22) Filed: Jan. 3, 2008

(51) Int. Cl.
*A01H 5/00* (2006.01)

(52) U.S. Cl. ..... Plt./263.1
(58) Field of Classification Search ..... Plt./263.1, Plt./263
See application file for complete search history.

*Primary Examiner*—Annette H Para
(74) *Attorney, Agent, or Firm*—John D. Fado; G. Byron Stover

(57) ABSTRACT

The present invention is a new and distinct pepper plant known as *Capisum annuum* L. '06C84', which displays a unique prostrate, indeterminate, spreading growth habit unlike that of the standard pepper plants. Plants of '06C84', are characterized by black foliage, numerous small round solitary black fruits that mature red, and a vigorous low prostrate growth habit.

3 Drawing Sheets

Genus and species of the claimed plant: *Capisum annuum.*
Variety denomination: '06C84'.

FIELD OF THE INVENTION

This invention concerns a new and distinct pepper plant known as *Capisum annuum* L. '06C84'.

DESCRIPTION OF RELATED PRIOR ART

Several commercial ornamental peppers are known. Ornamental peppers range in size and shape from short, compact plants with piquin sized fruits, such as 'Holiday Cheer', to plants as tall as 1 meter with full sized fruits, such as 'NuMex Mirasol'. Nearly all ornamental peppers have been primarily developed based upon unique fruit characteristics. '06C84' may be distinguished from all of the ornamental peppers known to us based upon its unique plant habitat. '06C84'has a prostrate, indeterminate, spreading growth habit. Other peppers may be dwarf, such as 'Holiday Cheer' and 'Medusa', but are compact and not spreading.

The characteristics of '06C84' were compared to the most similar plant on the market-'Black Pearl' (Plant Variety Protection Certificate number 200500020). 'Black Pearl' plants are smaller (45 cm in diameter and 31 cm in height), with larger (8.2 cm in length and 3.5 cm in width) but similar shaped (simple, entire, symmetrical, and lanceolate with an apiculate tip) leaves and leaf color (Royal Horticultural Society Colour Chart number 202A). Flowers of 'Black Pearl' are similar in size (average 2.1 cm) and color (Royal Horticultural Society Colour Chart number 81A) to '06C84'. Fruit of 'Black Pearl' are very different in fruit shape (round and average 1.6 cm in diameter) and mature fruit color (Royal Horticultural Society Colour Chart number 46A) and are borne in clusters (5–7 fruit per cluster).

ORIGIN OF THE NEW PLANT

The pepper plant originated from a controlled cross at the United States Department of Agriculture's Agricultural Research Service greenhouses in Beltsville, Md. '06C84' is an $F_1$ selection derived from initial crosses between the USDA pepper release '90C44', a selection from the heirloom tabasco-type pepper 'Royal Black', and the heirloom ornamental round-fruited type pepper 'Christmas Cheer'. The pedigree is complex (FIG. 1) and none of the parents were protected. '06C84' recombines many different characteristics from all of the different parents and does not resemble any single parent. For example plants of 'Christmas Cheer' produce round yellow fruit that ripen red on green foliaged plants; while plants of 'Royal Black' produce tabasco shape immature fruit that ripen to red on variegated green and purple foliaged plants. '90C44' was derived from interbreeding a diverse collection of small-fruited pungent germplasm from India. Most of the seedlings in this cross had green to purple variegated foliage. '90C44' was unique among the progeny in having solid purple foliage. The genes for the black foliage of '06C84' were derived from intercrosses of '90C44' and 'Royal Black'. Prostrate growth habit and round fruit shape are derived from 'Christmas Cheer'. Early generation selections focused on prostrate growth habit, followed by recurrent selection for intensity of black foliage pigmentation. '06C84' has a very unique prostrate and spreading grown habit combined with black foliage.

SUMMARY OF THE NEW PLANT

This application relates to a new and distinct pepper plant, known as *Capisum annuum* '06C84'. The following characteristic is outstanding. When compared to all other pepper plants known to us, '06C84' has a unique combination of indeterminate and prostrate growth habitat combined with black foliage.

The following characteristics are useful in distinguishing this plant and can be useful for plant identification:

1. Plants produce greater than three basal shoots that grow laterally, instead of upright forming a vigorous low prostrate growth habit (39 cm height and 98 cm diameter).

2. Plants produce numerous small round (1.2 cm) upright oriented solitary black fruits that mature red.
3. Plants produce black foliage.

BRIEF DESCRIPTION OF THE PHOTOGRAPHS

The accompanying photographs show typical characteristics of the new plant.

DESCRIPTION OF THE NEW PLANT

Figure 1:
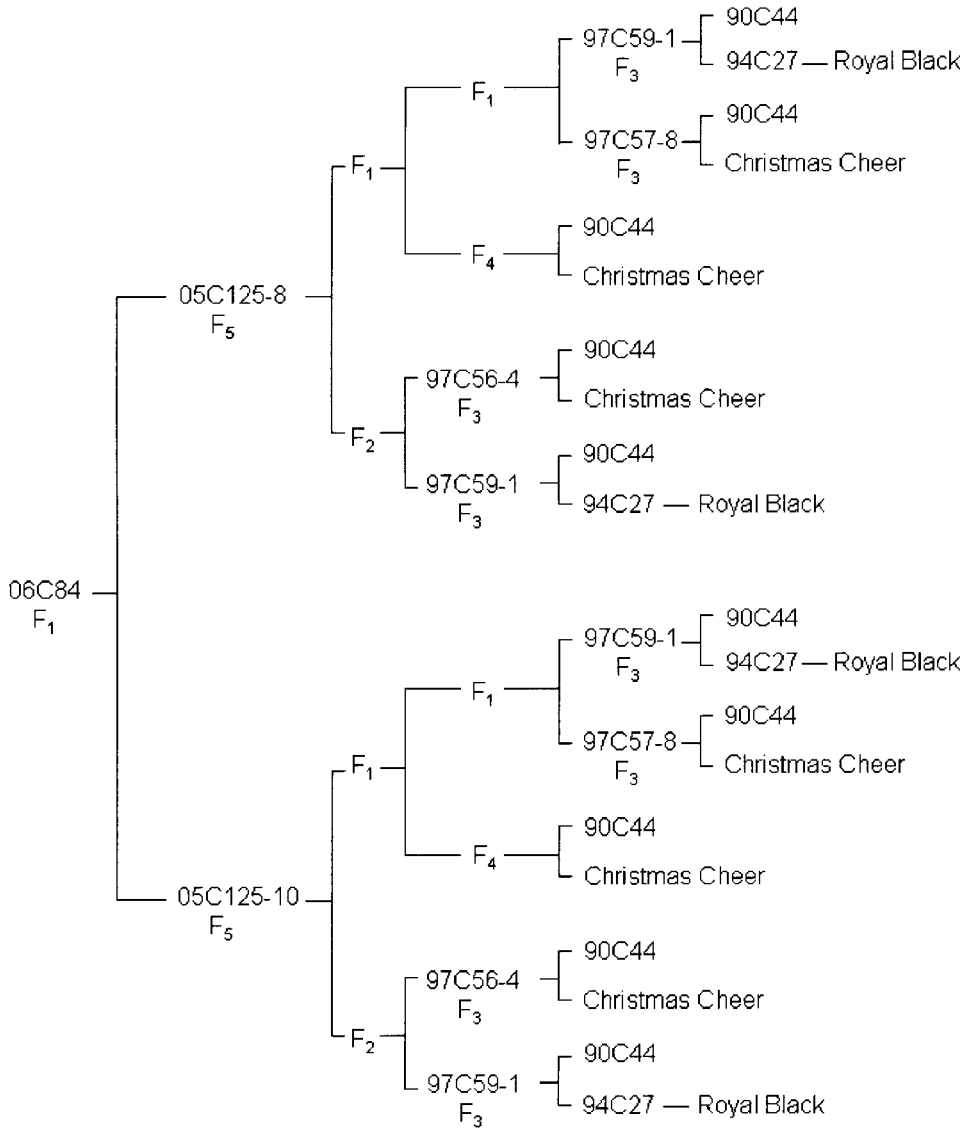
FIG. 1 shows the parentage of '06C84'.
Figure 2:
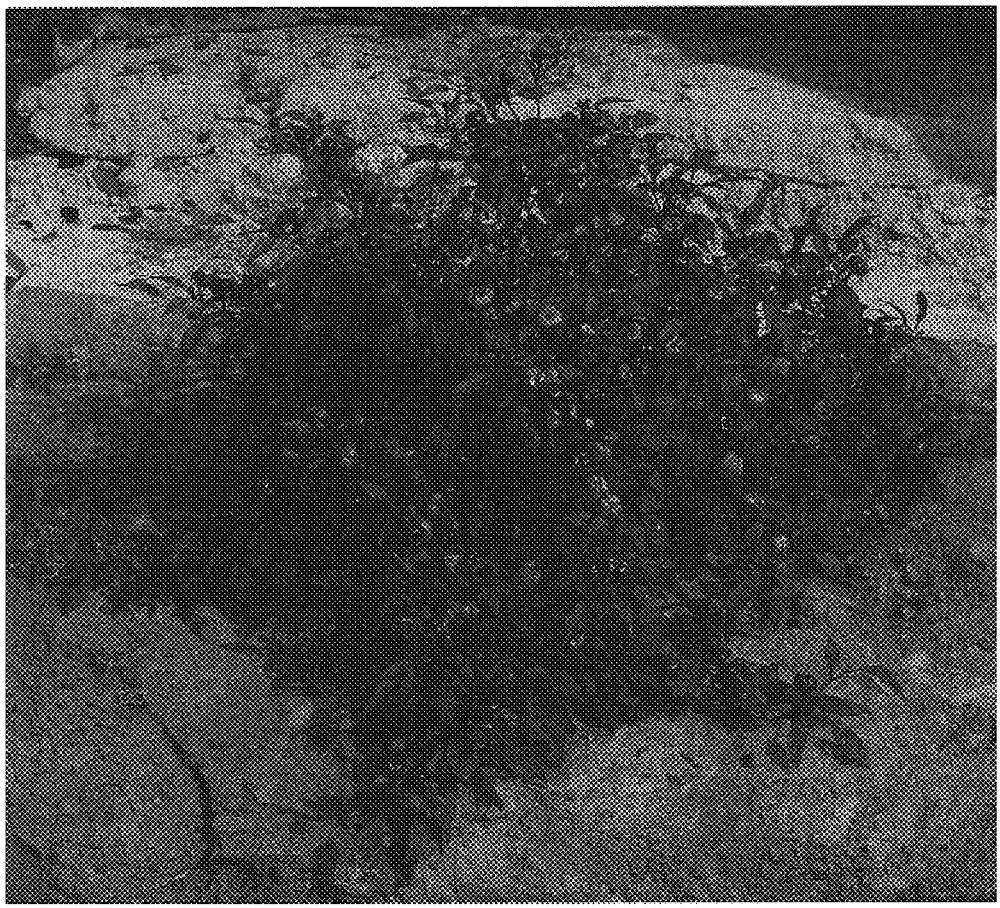
FIG. 2 shows a mature plant of '06C84' in September 2007.
Figure 3:
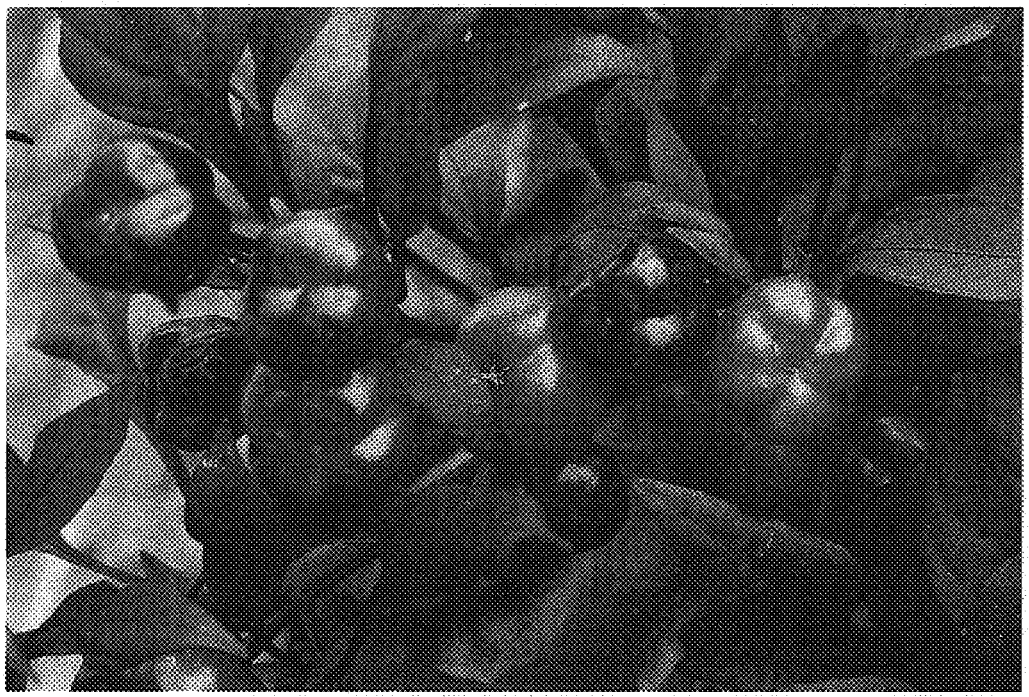
FIG. 3 shows mature red and immature black fruit and black leaves.

The following is a detailed description of the new plant, together with the plant's morphological characteristics. The characteristics of the plant were compared to the similar 'Black Pearl' (HortScience, 40:1571-1573). The description is based upon plants grown in the field at Beltsville, Md. about 90 days post-transplanting.

'06C84' is a diploid (2n=2x=24) herbaceous annual. '06C84' has performed uniformly in multiple trials. Leaves and stems are glabrous and glossy. Leaves are simple, entire, symmetrical, and lanceolate with an apiculate tip. Mature leaves average 4.5 cm in length (range: 4.0 to 5.0 cm) and 2.4 cm in width (range: 2.3 to 2.5 cm). Petiole length averages 2.1 cm (range: 2.0 to 2.2 cm). Adaxial leaf surface is black (Royal Horticultural Society Colour Chart number 202A). 'Black Pearl' has larger, but similar shaped and colored leaves. 'Black Pearl' leaves average 8.2 cm in length (range: 7.4 to 11.0 cm) and 3.5 cm in width (range: 2.9 to 4.5 cm).

The plant habit of '06C84' is unique. Unlike the growth habit of all ornamental peppers known to us, '06C84' has a vigorous prostrate and indeterminate habit. Plants average 98 cm in diameter (range: 93 to 102 cm) and 39 cm in height (range: 38 to 43 cm). While 'Black Pearl' plants average 45 cm in diameter (range: 44 to 47 cm) and 31 cm in height (range: 29 to 34 cm).

'06C84' flowers are self-compatible, hermaphroditic, pentamerous and hypogynous. The purple flowers (Royal Horticultural Society Colour Chart number 81A) average 1.5 cm in diameter (range: 1.3 to 1.8 cm) and have purple filaments and styles. Flowers of 'Black Pearl' are similar.

'06C84' fruits are solitary and are borne upright. There are approximately 738 fruit per plant and an average of 33 seed per fruit (range: 30 to 36). Immature fruits are black (Royal Horticultural Society Colour Chart number 202A) and mature to red (Royal Horticultural Society Colour Chart number 46A). Fruits are globe shaped and average 1.2 cm in diameter (range: 1.0 to 1.3 cm). The upright pedicels average 1.6 cm (range: 1.4 to 2.0 cm). Fruit are extremely pungent. Since '06C84' is intended for ornamental applications, Scoville pungency units were not determined. Fruit of 'Black Pearl' are similar in shape and color, but are larger and borne in clusters of 6 to 8. 'Black Pearl' fruit average 1.6 cm in diameter (range: 1.3 to 1.7 cm).

Typical of *C. annuum,* '06C84' is a warm-season crop requiring minimum daytime temperatures of 18 to 21 C. Optimal growth is achieved at higher temperatures up to 32 C. Plants grow poorly in the 5 to 15 C range and are frost-susceptible. Like most peppers, '06C84' is field tolerant to most pests and diseases, e.g., Fusarium wilt, verticillium wilt, aphids, and mites, based on field reaction, not in controlled testing.

'06C84' has been asexually reproduced by vegetative shoot cuttings over successive generations since 2005. Over that period no off-type of '06C84' has been observed or reported to us. Thus it is concluded that '06C84' is stable and reproduced true to type in successive generations of asexual reproduction. Plants were propagated at Beltsville, Md. and Dearing, Ga.

References

Royal Horticultural Society. 1966. Royal Horticultural Society colour chart. Royal Hort. Soc., London, UK.

Stommel, J. R. and P. W. Bosland. 2006. Pepper, Ornamental, *Capsicum annuum,* p. 561–599. In: Anderson, N. O. (ed.). Flower breeding and genetics: Issues, challenges and opportunities for the 21st century. Springer, Dordrecht, The Netherlands.

Stommel, J. R. and R. G. Griesbach. 1993. New ornamental Capsicum germplasm: Lines 90C40, 90C44, and 90C53. HortScience 28:858–859.

Stommel, J. R. and R. G. Griesbach. 2005. *Capsicum annuum* L. 'Black Pearl'. HortScience 40:1571–1573.

What is claimed is:

1. A new and distinct pepper plant known as '06C84' as described herein, illustrated and identified by the characteristics set forth above.

* * * * *